(12) United States Patent
Li et al.

(10) Patent No.: US 10,401,306 B2
(45) Date of Patent: Sep. 3, 2019

(54) COMBINED IMAGE GENERATION OF ARTICLE UNDER EXAMINATION AND IMAGE OF TEST ITEM

(71) Applicant: ANALOGIC CORPORATION, Peabody, MA (US)

(72) Inventors: Zhaolin Li, Malden, MA (US); David Lieblich, Worcester, MA (US)

(73) Assignee: Analogic Corporation, Peabody, MA (US)

(*) Notice: Subject to any disclaimer, the term of this patent is extended or adjusted under 35 U.S.C. 154(b) by 109 days.

(21) Appl. No.: 15/571,933

(22) PCT Filed: May 7, 2015

(86) PCT No.: PCT/US2015/029591
§ 371 (c)(1),
(2) Date: Nov. 6, 2017

(87) PCT Pub. No.: WO2016/178682
PCT Pub. Date: Nov. 10, 2016

(65) Prior Publication Data
US 2018/0106733 A1 Apr. 19, 2018

(51) Int. Cl.
*G06K 9/00* (2006.01)
*G01N 23/04* (2018.01)
(Continued)

(52) U.S. Cl.
CPC .......... *G01N 23/046* (2013.01); *G06T 11/006* (2013.01); *G06T 11/008* (2013.01);
(Continued)

(58) Field of Classification Search
USPC ....... 382/100, 103, 106, 129, 131, 154–155, 382/162, 168, 172–173, 181, 189–199,
(Continued)

(56) References Cited

U.S. PATENT DOCUMENTS

| 2010/0046704 | A1* | 2/2010 | Song | G01N 23/04 |
| | | | | 378/57 |
| 2012/0243741 | A1* | 9/2012 | Shet | G06K 9/6296 |
| | | | | 382/103 |

(Continued)

FOREIGN PATENT DOCUMENTS

WO 2013/165396 A1 11/2013

OTHER PUBLICATIONS

Patent Cooperation Treaty (PCT) International Search Report and Written Opinion issued for PCT International Application No. PCT/US2015/029591 having an International Filing Date of May 7, 2017 dated Feb. 10, 2016 (14 pgs).

(Continued)

*Primary Examiner* — Seyed H Azarian
(74) *Attorney, Agent, or Firm* — TraskBritt

(57) ABSTRACT

Among other things, one or more techniques and/or systems for generating a three-dimensional combined image is provided. A three-dimensional test image of a test item is combined with a three-dimensional article image of an article that is undergoing a radiation examination to generate the three-dimensional combined image. A first selection region of the three-dimensional article image is selected. The three-dimensional test image of the test item is inserted within the first selection region. Although the test item is not actually comprised within the article under examination, the three-dimensional combined image is intended to cause the test item to appear to be comprised within the article.

19 Claims, 11 Drawing Sheets

(51) Int. Cl.
  *G01N 23/046* (2018.01)
  *G06T 11/00* (2006.01)
  *G06T 17/00* (2006.01)
  *G06T 19/20* (2011.01)

(52) U.S. Cl.
  CPC .............. *G06T 17/00* (2013.01); *G06T 19/20* (2013.01); *G06T 2211/408* (2013.01); *G06T 2211/424* (2013.01); *G06T 2211/436* (2013.01); *G06T 2219/2004* (2013.01); *G06T 2219/2021* (2013.01)

(58) Field of Classification Search
  USPC ............... 382/209, 224, 232, 254, 274, 276, 382/283–291, 305, 312, 318, 220; 378/4, 378/21, 57
  See application file for complete search history.

(56) References Cited

U.S. PATENT DOCUMENTS

2014/0161333 A1* 6/2014 Litvin .................. G01N 23/046
    382/131
2014/0241495 A1* 8/2014 Gudmundson ........ G01N 23/04
    378/57
2015/0104089 A1* 4/2015 Litvin .................. G06T 11/006
    382/131

OTHER PUBLICATIONS

Najla Megherbi et al.: "Fully Automatic 3D Threat Image Projection: Application to Densely Cluttered 3D Computer Tomography Baggage Images," Image Processing Theory, Tools and Application (IPTA), 2012 3rd International Conference on, IEEE, Oct. 15, 2012 (8 pgs).

Mark Mitckes: "Thread Image Projection—An Overview," Internet Citation Oct. 1, 2003, (24 pgs).

Najla Megherbi, et al.: "Radon Transformation Based Automatic Metal Artefacts Generation for 3D Threat Image Projection," Proceedings of SPIE, vol. 8901, Oct. 16, 2013, (10 pgs).

Yesna O. Yildiz, et al.: "3D Threat Image Projection," Proceedings of SPIE, S P I E—International Society for Optical Engineering, US, vol. 6805, Jan. 28, 2008 (8 pgs).

* cited by examiner

COMBINED IMAGE GENERATION OF ARTICLE UNDER EXAMINATION AND IMAGE OF TEST ITEM

BACKGROUND

The present application relates to the field of radiation imaging. It finds particular application with computed-tomography (CT) security scanners configured to generate a three-dimensional image of an article under examination. It also relates to medical, security, and other applications where the identification of articles using radiation technology (e.g., x-ray systems, gamma-ray systems, etc.) may be useful.

Imaging systems (e.g., also referred to as radiation imaging systems) such as computed tomography (CT) systems, diffraction CT, single-photon emission computed tomography (SPECT) systems, digital projection systems, and/or line systems, for example, are utilized to provide information, or images, of interior aspects of an article under examination. Generally, the article is exposed to radiation comprising photons (e.g., such as x-ray photons, gamma ray photons, etc.), and an image(s) is formed based upon the radiation absorbed and/or attenuated by interior aspects of the article, or rather an amount of photons that is able to pass through the article. Generally, highly dense aspects of the article absorb and/or attenuate more radiation than less dense aspects, and thus an aspect having a higher density, such as a bone or metal, for example, may be apparent when surrounded by less dense aspects, such as muscle or clothing.

Imaging systems are utilized in a variety of fields to image aspects of an article not readily visible to the naked eye. For example, imaging systems are used in security applications to identify potential threat items, which may include weapons and/or explosives, concealed within a suitcase, bag, person, and/or other article, for example. While automated threat detection systems are available in some imaging systems, oftentimes it is the responsibility of an operator viewing an image of an article to determine whether the article contains a potential threat item (e.g., and thus requires additional inspections, such as a hands-on inspection). Accordingly, operators at security checkpoints and other venues are required to be attentive. Such attentiveness, combined with the knowledge that few articles actually contain a threat item, may lead to fatigue and/or other distractions that potentially result in an article containing a threat item passing through the system undetected.

SUMMARY

Aspects of the present application address the above matters, and others. According to one aspect, a method for generating a three-dimensional combined image representative of an article undergoing a radiation examination and representative of a test item not comprised within the article during the radiation examination is provided. The method comprises acquiring a three-dimensional article image of the article via the radiation examination and acquiring a three-dimensional test image of the test item. The method comprises identifying, within the three-dimensional article image, a first group of voxels representative of object regions corresponding to objects within the article and a second group of voxels representative of void regions corresponding to voids within the article. The method comprises selecting a first selection region of the three-dimensional article image within which to insert the three-dimensional test image and determining a degree of overlap between the first selection region and the first group of voxels. The method comprises, when the degree of overlap is less than a specified degree, merging the three-dimensional test image with the three-dimensional article image to generate the three-dimensional combined image, where the three-dimensional combined image is representative of the test item being within the article at the first selection region during the radiation examination. The method comprises, when the degree of overlap is greater than the specified degree, selecting a second selection region of the three-dimensional article image within which to insert the three-dimensional test image.

According to another aspect, a method for generating a three-dimensional combined image representative of an article undergoing a radiation examination and representative of a test item not comprised within the article during the radiation examination is provided. The method comprises acquiring a three-dimensional article image of the article via the radiation examination and acquiring a three-dimensional test image of the test item. The method comprises identifying, within the three-dimensional article image, a first group of voxels representative of object regions corresponding to objects within the article and a second group of voxels representative of void regions corresponding to voids within the article. The method comprises selecting a first selection region of the three-dimensional article image within which to insert the three-dimensional test image and determining a degree of overlap between the first selection region and the first group of voxels. The method comprises, when the degree of overlap is less than a specified degree, determining a number of voxels within the first group of voxels that abut the first selection region. The method comprises, when the number of voxels exceeds a threshold, merging the three-dimensional test image with the three-dimensional article image to generate the three-dimensional combined image, where the three-dimensional combined image is representative of the test item being within the article at the first selection region during the radiation examination.

According to yet another aspect, a method for generating a three-dimensional combined image representative of an article undergoing a radiation examination and representative of a test item not comprised within the article during the radiation examination is provided. The method comprises acquiring a three-dimensional article image of the article via the radiation examination and acquiring a three-dimensional test image of the test item. The method comprises identifying, within the three-dimensional article image, a first group of voxels representative of object regions corresponding to objects within the article and a second group of voxels representative of void regions corresponding to voids within the article. The method comprises selecting a first selection region of the three-dimensional article image within which to insert the three-dimensional test image and determining whether a portion of the first group of voxels are within an outer boundary region of the first selection region or an inner boundary region of the first selection region. The method comprises, when the portion of the first group of voxels are within the outer boundary region of the first selection region, merging the three-dimensional test image with the three-dimensional article image to generate the three-dimensional combined image, where the three-dimensional combined image is representative of the test item being within the article at the first selection region during the radiation examination.

According to yet another aspect, an imaging system is provided. The imaging system comprises a radiation source configured to expose an article to radiation and a detector array configured to detect at least some of the radiation. The imaging system comprises an image generator configured to generate a three-dimensional article image of the article based upon the at least some of the radiation detected by the detector array. The imaging system comprises an image insertion component configured to identify, within the three-dimensional article image, a first group of voxels representative of object regions corresponding to objects within the article and a second group of voxels representative of void regions corresponding to voids within the article. The image insertion component is configured to select a first selection region of the three-dimensional article image within which to insert a three-dimensional test image of a test item, the test item not comprised within the article when the article is exposed to the radiation. The image insertion component is configured to determine a degree of overlap between the first selection region and the first group of voxels. When the degree of overlap is less than a specified degree, the image insertion component is configured to merge the three-dimensional test image with the three-dimensional article image to generate the three-dimensional combined image, where the three-dimensional combined image is representative of the test item being within the article when the article is exposed to the radiation. When the degree of overlap is greater than the specified degree, the image insertion component is configured to select a second selection region of the three-dimensional article image within which to insert the three-dimensional test image.

Those of ordinary skill in the art may appreciate still other aspects of the present application upon reading and understanding the appended description.

FIGURES

The application is illustrated by way of example and not limitation in the figures of the accompanying drawings, in which like references generally indicate like elements and in which.

Figure 3:
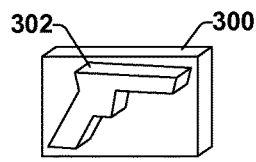
Figure 4:
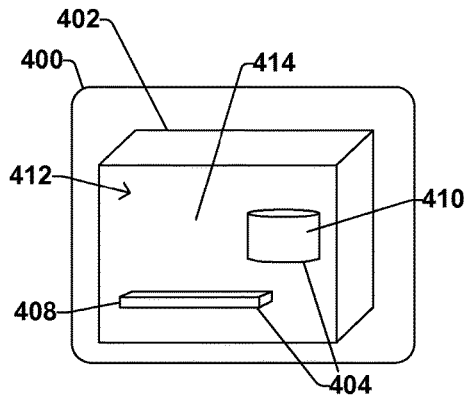
Figure 5:
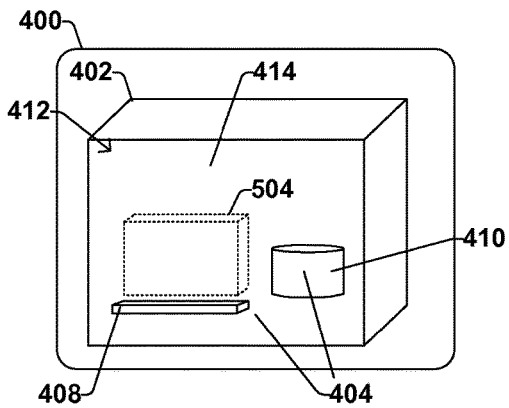
Figure 6:
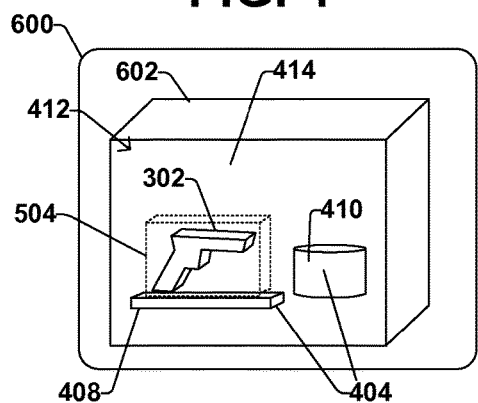
Figure 7:
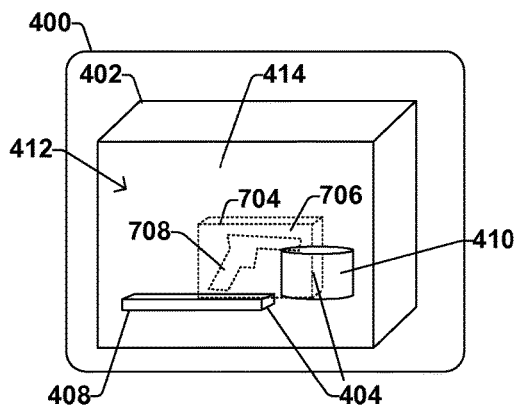
Figure 8:
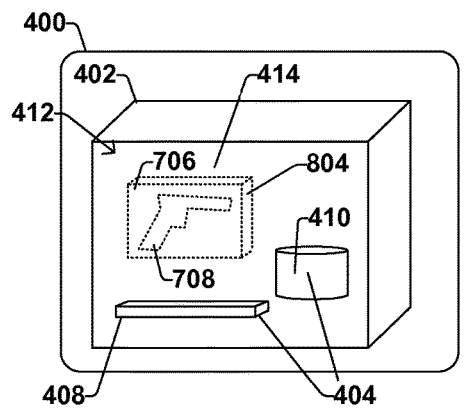

FIG. 3 illustrates an example 3D article image.
FIG. 4 illustrates an example 3D article image.
FIG. 5 illustrates an example 3D article image.
FIG. 6 illustrates an example 3D article image.
FIG. 7 illustrates an example 3D article image.
FIG. 8 illustrates an example 3D article image.

Figure 9:
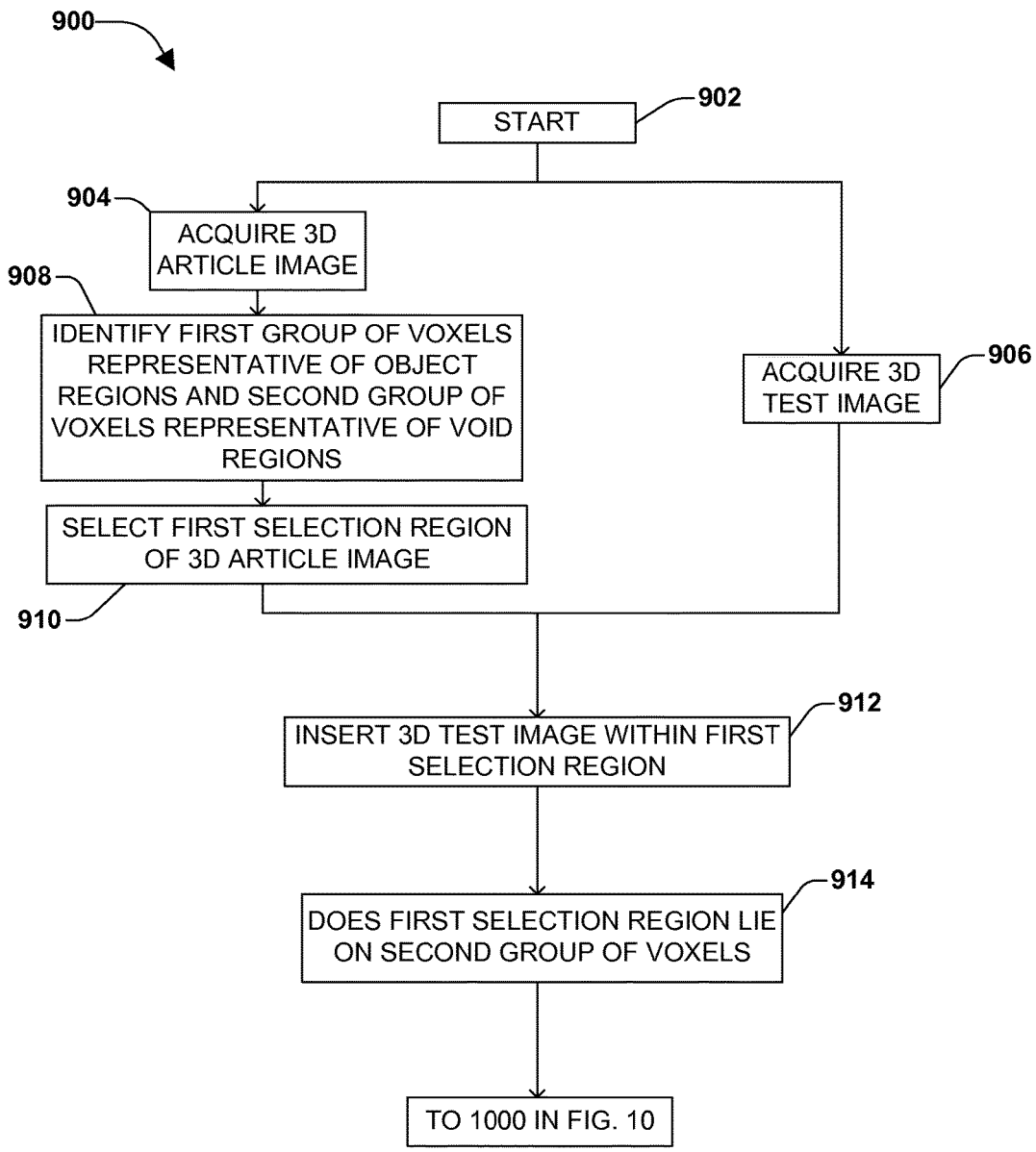

FIG. 9 is a flow chart diagram of an example method for generating a three-dimensional combined image representative of an article undergoing examination and representative of a test item.

Figure 10:
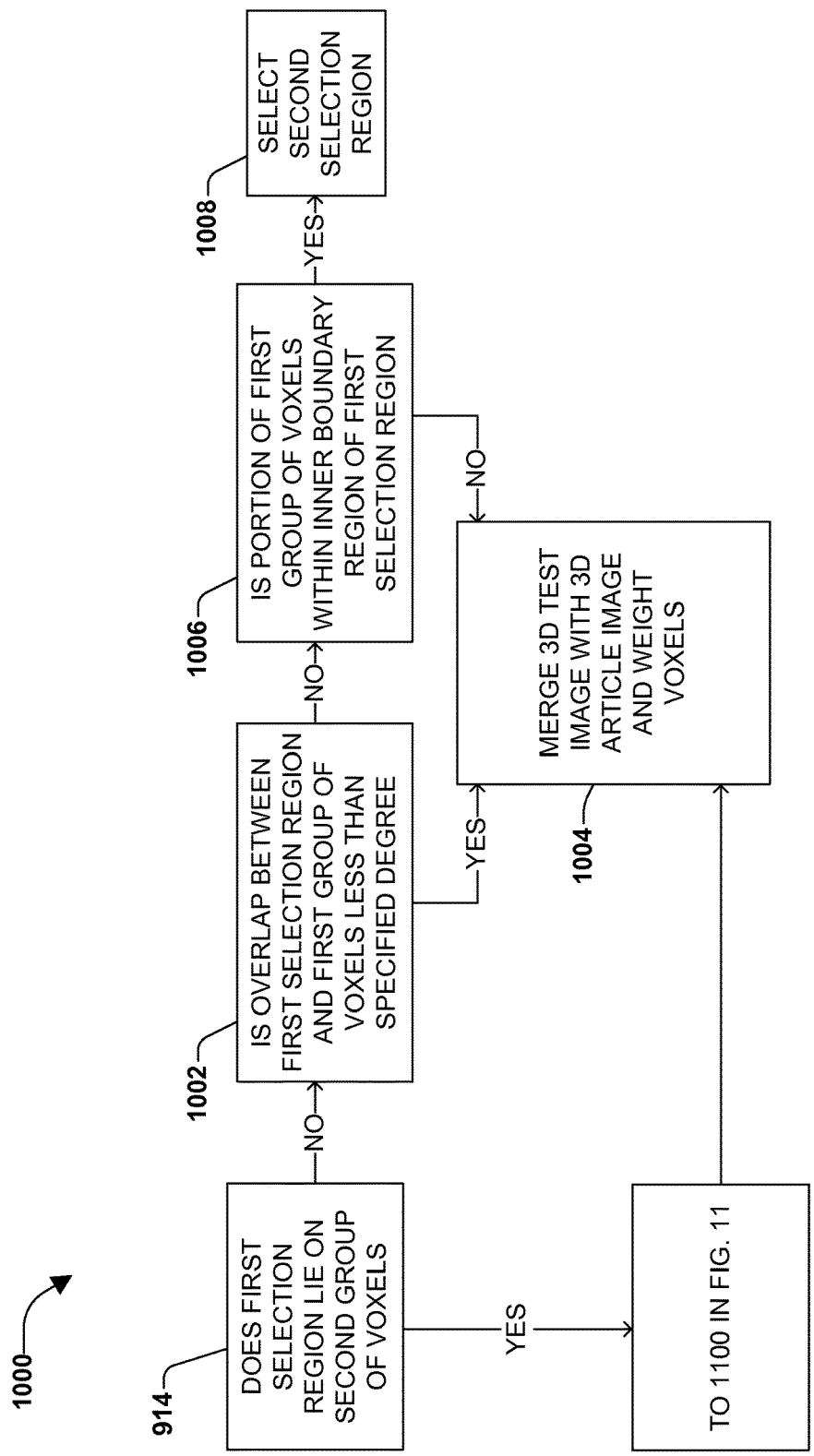

FIG. 10 is a flow chart diagram of an example method for generating a three-dimensional combined image representative of an article undergoing examination and representative of a test item.

Figure 11:
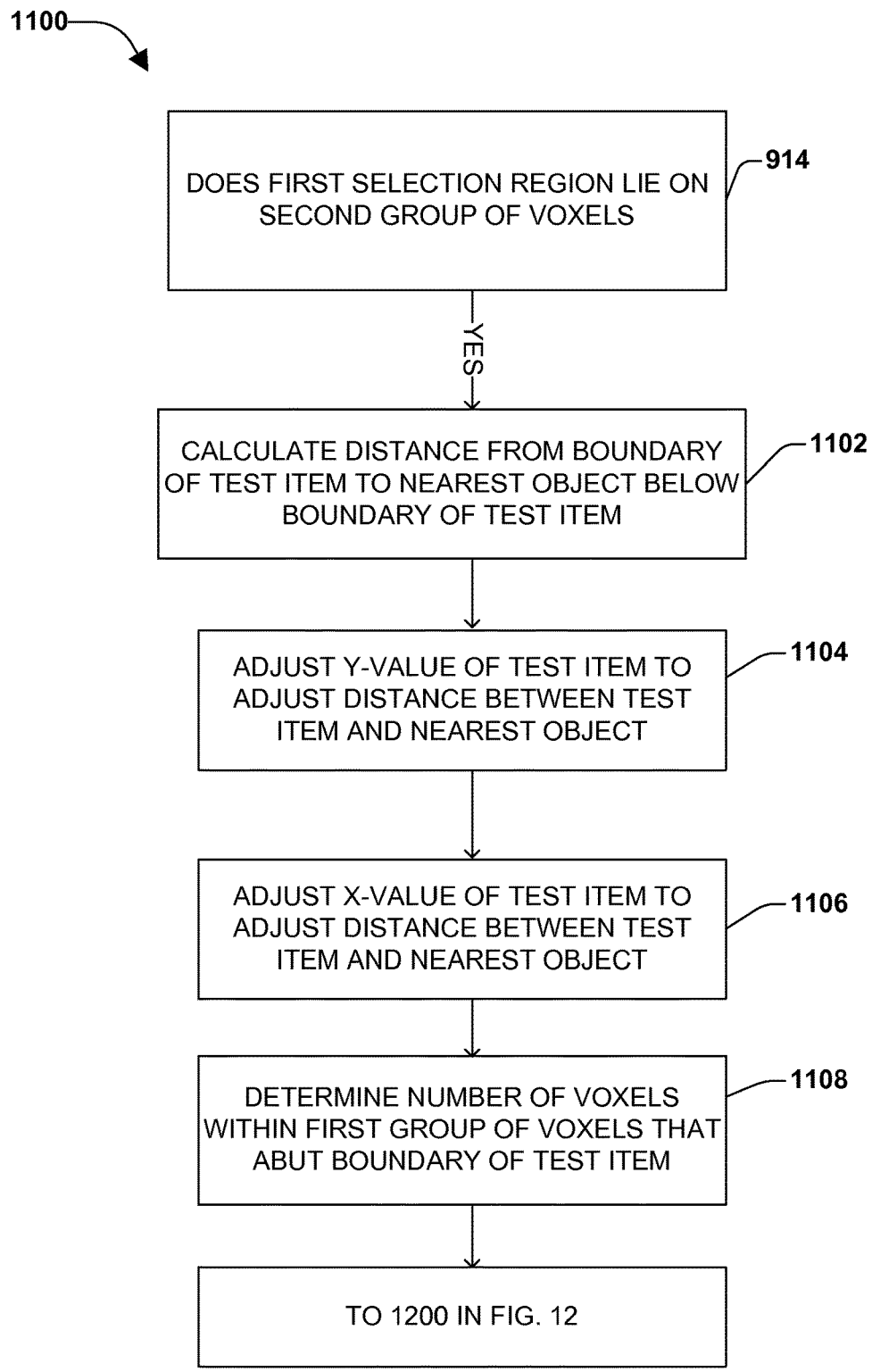

FIG. 11 is a flow chart diagram of an example method for generating a three-dimensional combined image representative of an article undergoing examination and representative of a test item.

Figure 12:
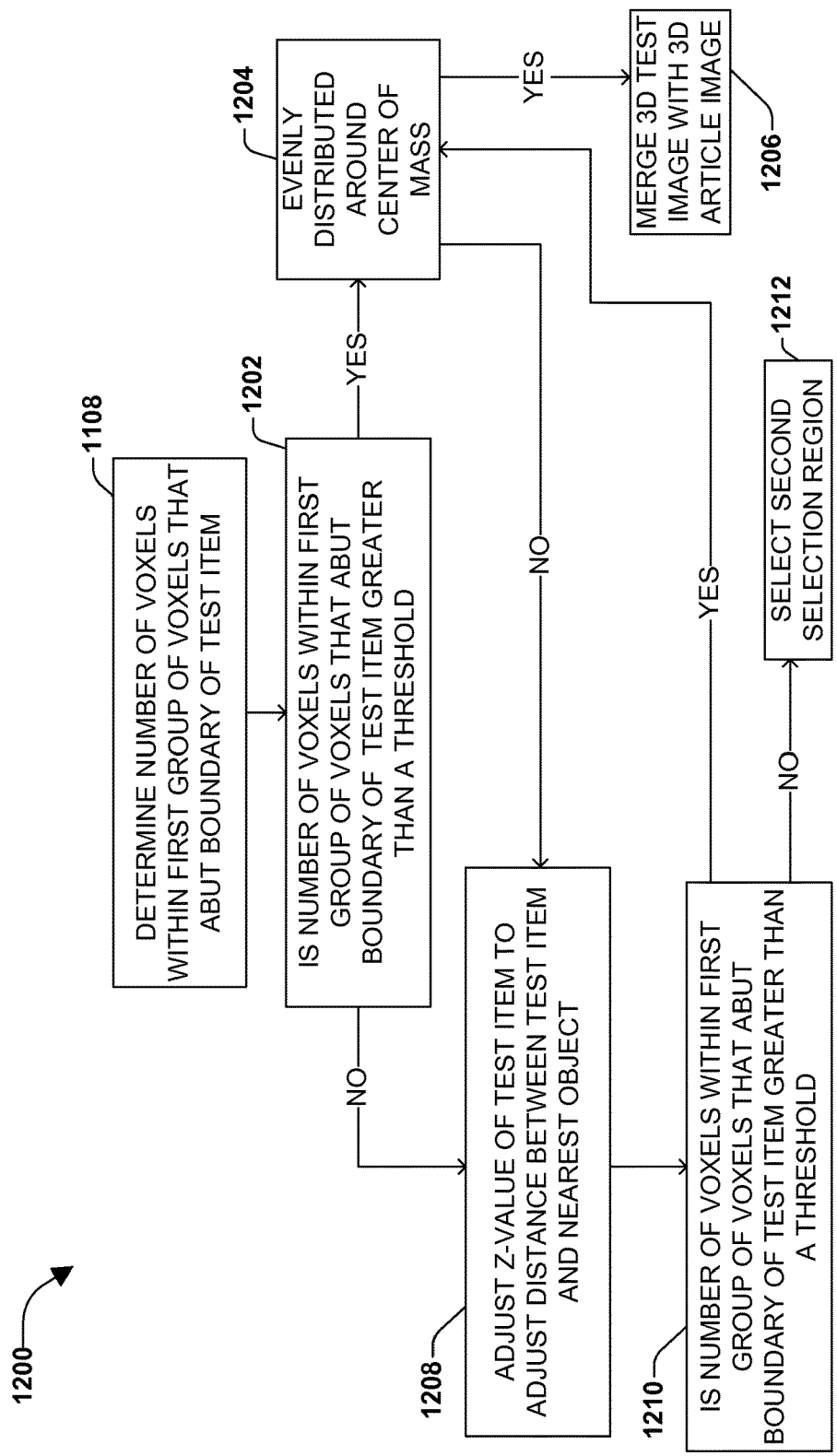

FIG. 12 is a flow chart diagram of an example method for generating a three-dimensional combined image representative of an article undergoing examination and representative of a test item.

Figure 13:
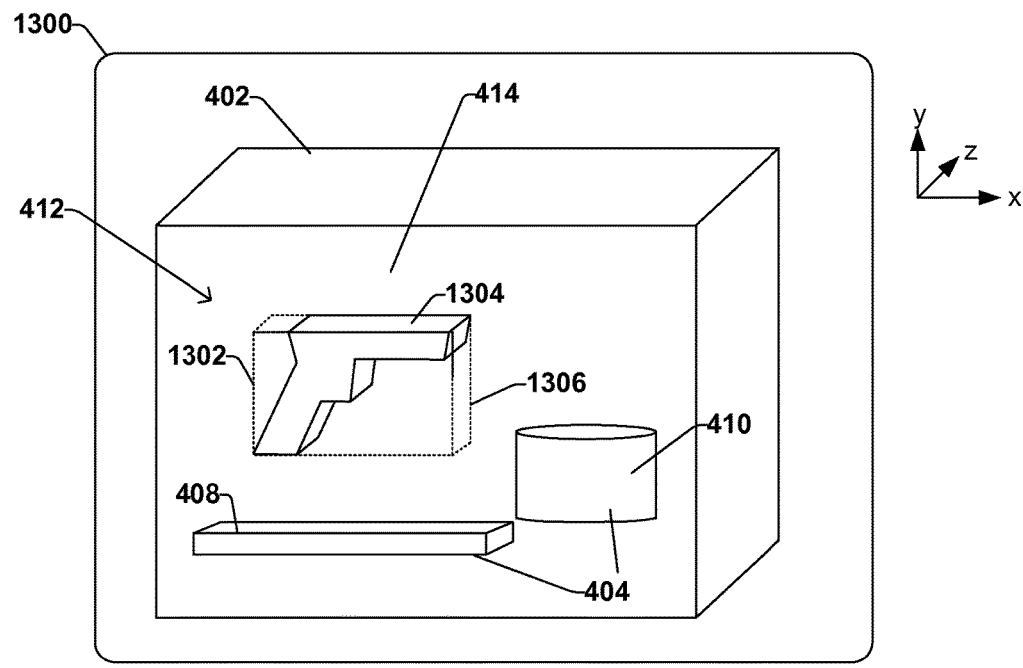
Figure 14:
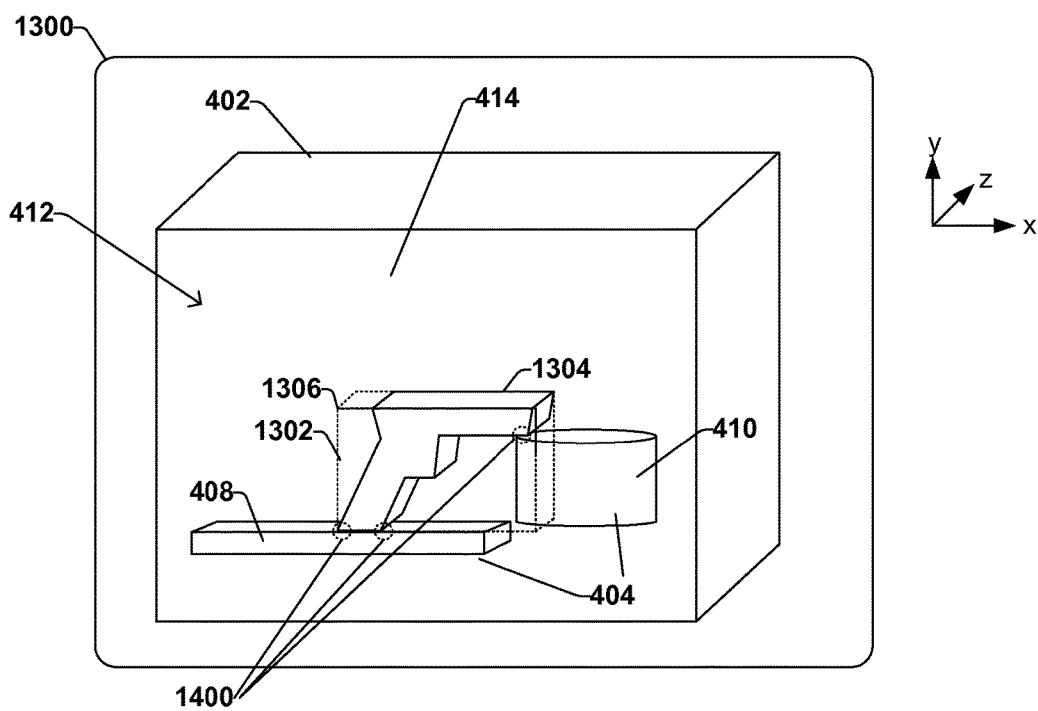

FIG. 13 illustrates an example 3D article image.
FIG. 14 illustrates an example 3D article image.

Figure 15:
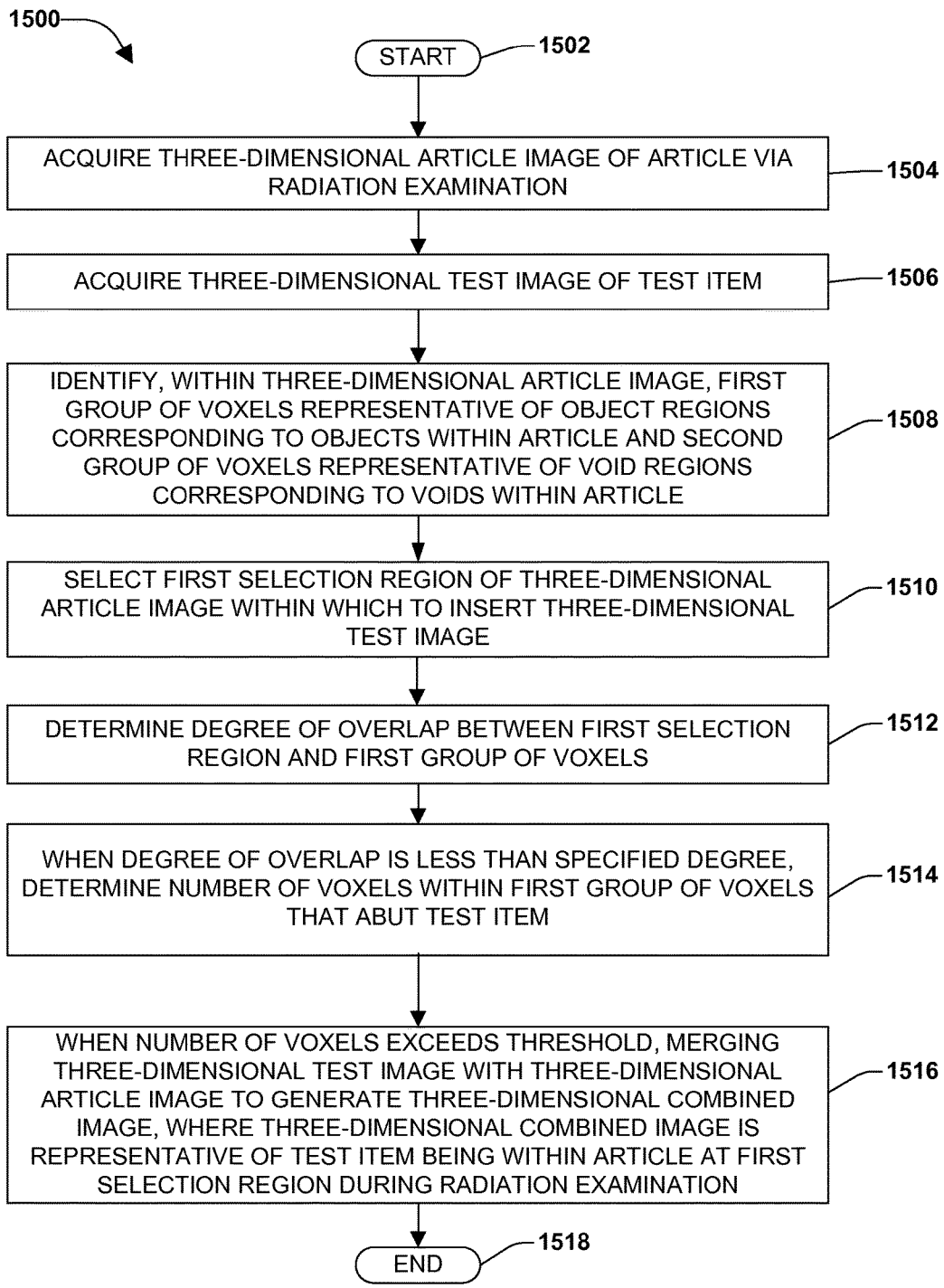

FIG. 15 is a flow chart diagram of an example method for generating a three-dimensional combined image representative of an article undergoing examination and representative of a test item.

Figure 16:
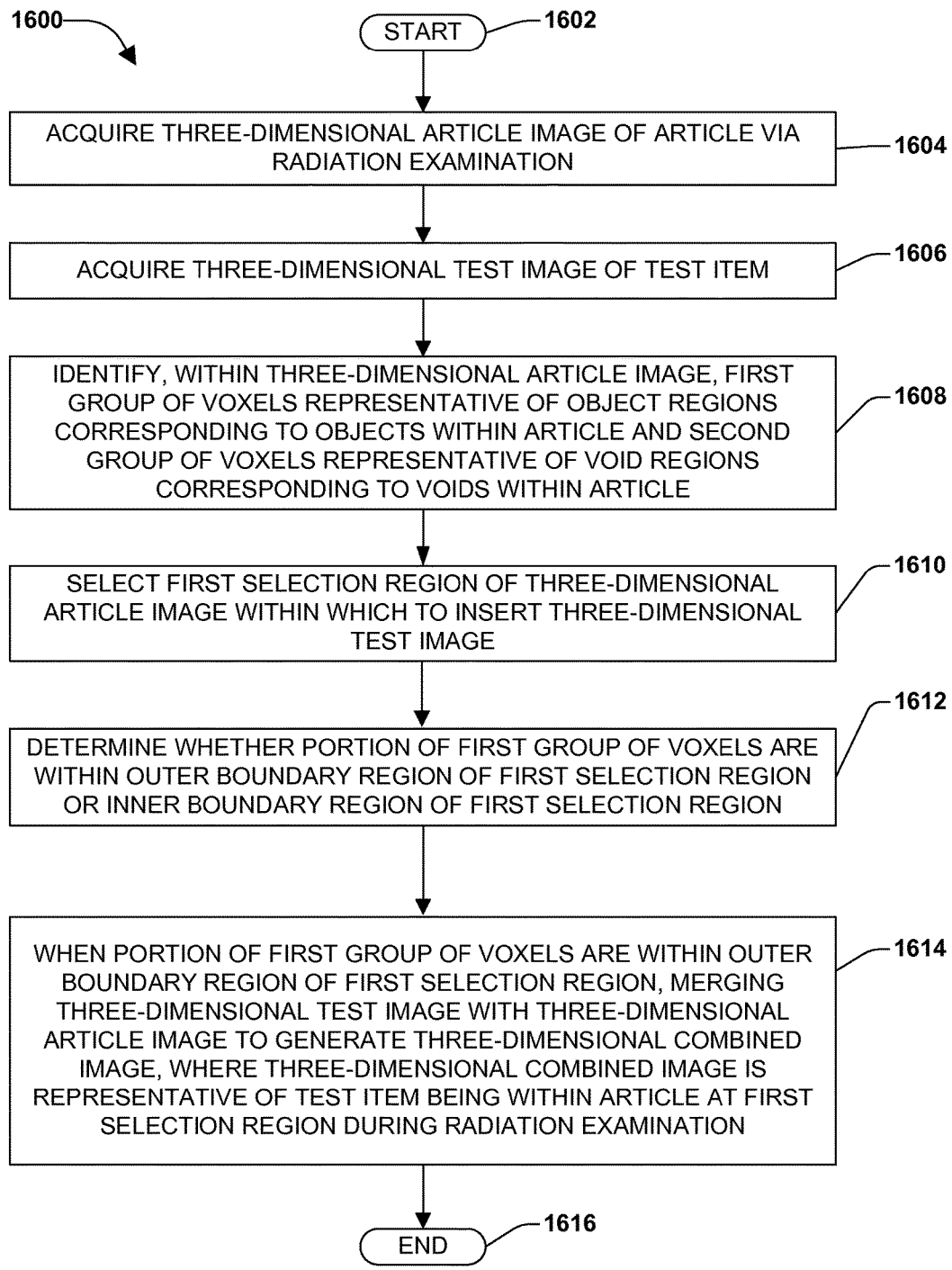

FIG. 16 is a flow chart diagram of an example method for generating a three-dimensional combined image representative of an article undergoing examination and representative of a test item.

Figure 17:
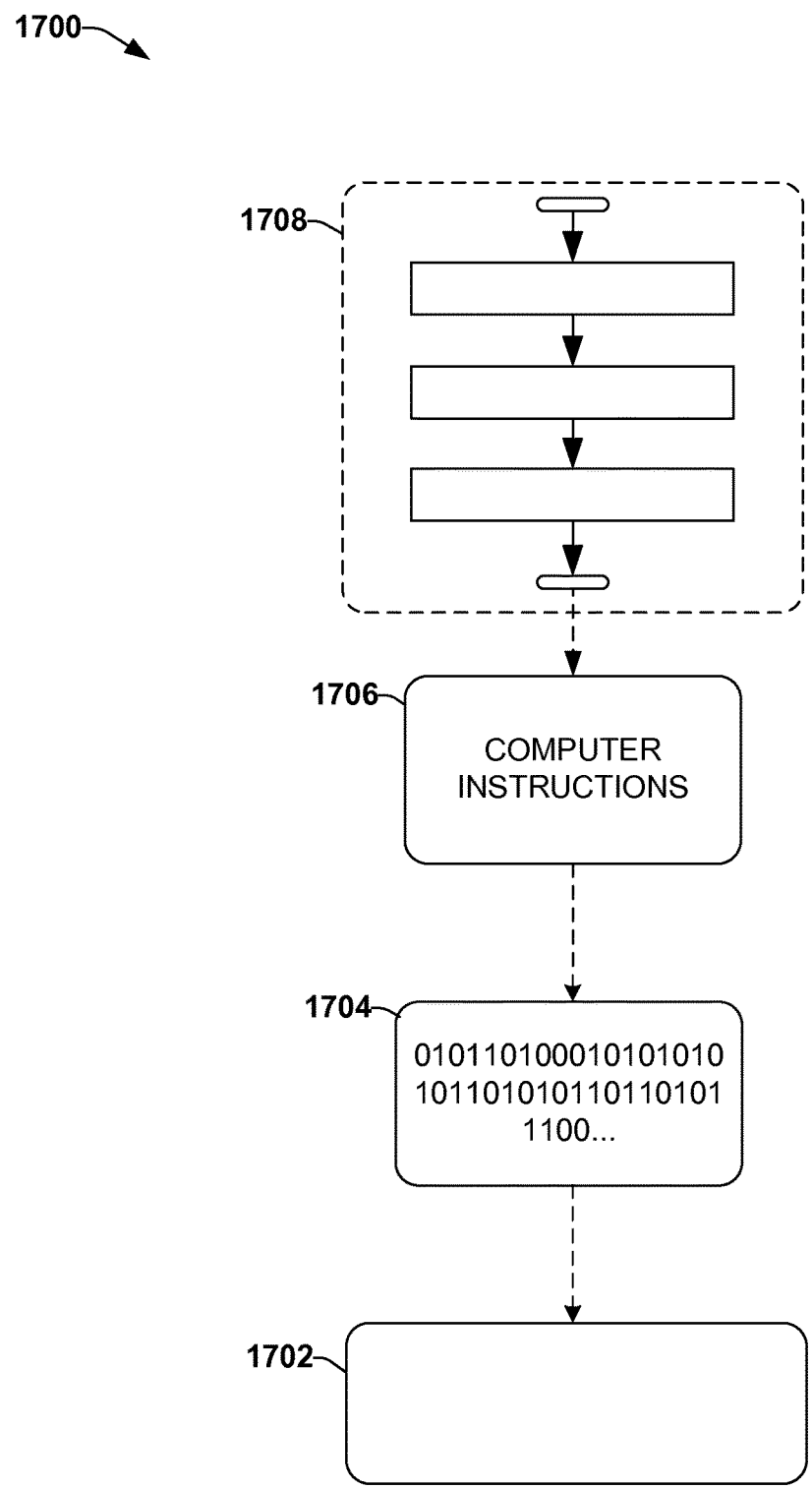

FIG. 17 is an illustration of an example computer-readable medium comprising processor-executable instructions configured to embody one or more of the provisions set forth herein.

DETAILED DESCRIPTION

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

Imaging systems that employ radiation (e.g., ionizing radiation such as x-rays, gamma rays, etc.) to generate images are utilized in a variety of applications, including for security purposes within transportation networks and/or other sensitive areas by imaging bags, suitcases, people, etc. (e.g., collectively referred to as articles). One example type of such an imaging system is a CT imaging system, which is configured to generate three-dimensional (3D) images of articles under examination and allows for automated and/or manual detection of potential threat items.

In a typical configuration, a CT imaging system presents an operator with 3D volumetric images and/or two-dimensional (2D) projections (e.g., projected from the 3D volumetric images) of articles in the imaged volume, which comprises a bin, bag, or other article conveyed through an examination region. The system may also perform automated detection of threat items, which may highlight suspected threat items. The operator is typically responsible for determining whether an additional inspection, such as a manual inspection, of the article is warranted.

The effectiveness and/or reliability of the operator may depend upon, among other things, training, level of fatigue, and/or presence of performance controls configured to evaluate, control, and/or maintain an operator's performance. Accordingly, a common approach to control and/or maintain operator performance is randomized testing. By way of example, test bags comprising test items that appear to be potential threat items may be intermingled with other bags on a conveyor belt for examination by the imaging system, and the operator's ability to correctly identify the test bag as containing a potential threat item may be measured. While such a technique is useful, it may be appreciated that there are a limited number of possible test bags and/or potential threat items at a particular security checkpoint, and thus operators may become familiarized with the test bags and/or potential threat items over time.

Accordingly, systems and/or techniques are described herein that provide for inserting a 3D test image of a test item (e.g., potential threat item) into a 3D article image of an article (e.g., such as a benign suitcase or other bag) to generate a 3D combined image. The 3D combined image represents both the test item and the article, and thus it appears as though the test item is comprised within the article (e.g., even though the test item was not comprised within the article when the article underwent an examination). A data structure may comprise a plurality (e.g., 10s, 100s, 1000s, etc.) of test item images, each representative of a different test item, and the 3D test image that is utilized may be selected at random, for example. In a possible example, a location and/or an orientation of the inserted test may also be at random. Moreover, in one embodiment, the particular article into which the test item is artificially inserted may be selected at random. Thus, it may be more difficult for operators to become familiarized with the articles and/or potential threat items, for example.

The 3D combined image may be derived by combining a 3D article image of the article under examination with a 3D test image of the test item (e.g., the threat item). By way of example, the 3D article image of the article may be analyzed to identify a first selection region that is substantially free of dense objects and/or objects having a density and/or atomic number higher than a specified density and/or atomic number threshold. The 3D test image of the test item can thereafter be artificially inserted into the first selection region to generate the 3D combined image.

It may be appreciated that while continued reference is made herein to CT systems employed in security applications, the instant disclosure, including the scope of the claims, is not intended to be limited to such embodiments (e.g., CT systems employed in security applications). For example, the systems and/or techniques provided for herein may find applicability in medical applications and/or industrial applications that utilize CT imaging systems and/or other imaging systems to generate images. By way of example, images of tumors and/or other abnormalities may be inserted into images of patients to test the ability of students, technicians, and/or doctors to identify the abnormalities.

Moreover, that instant application is not intended to be limited to use with a particular radiation measurement technique. For example, the systems and/or techniques described herein may find applicability to charge-integrating imaging systems, photon counting imaging systems, single-energy imaging systems, multi-energy (dual-energy) imaging systems, indirect conversion imaging systems, and/or direct conversion imaging systems, for example.

Figure 1:
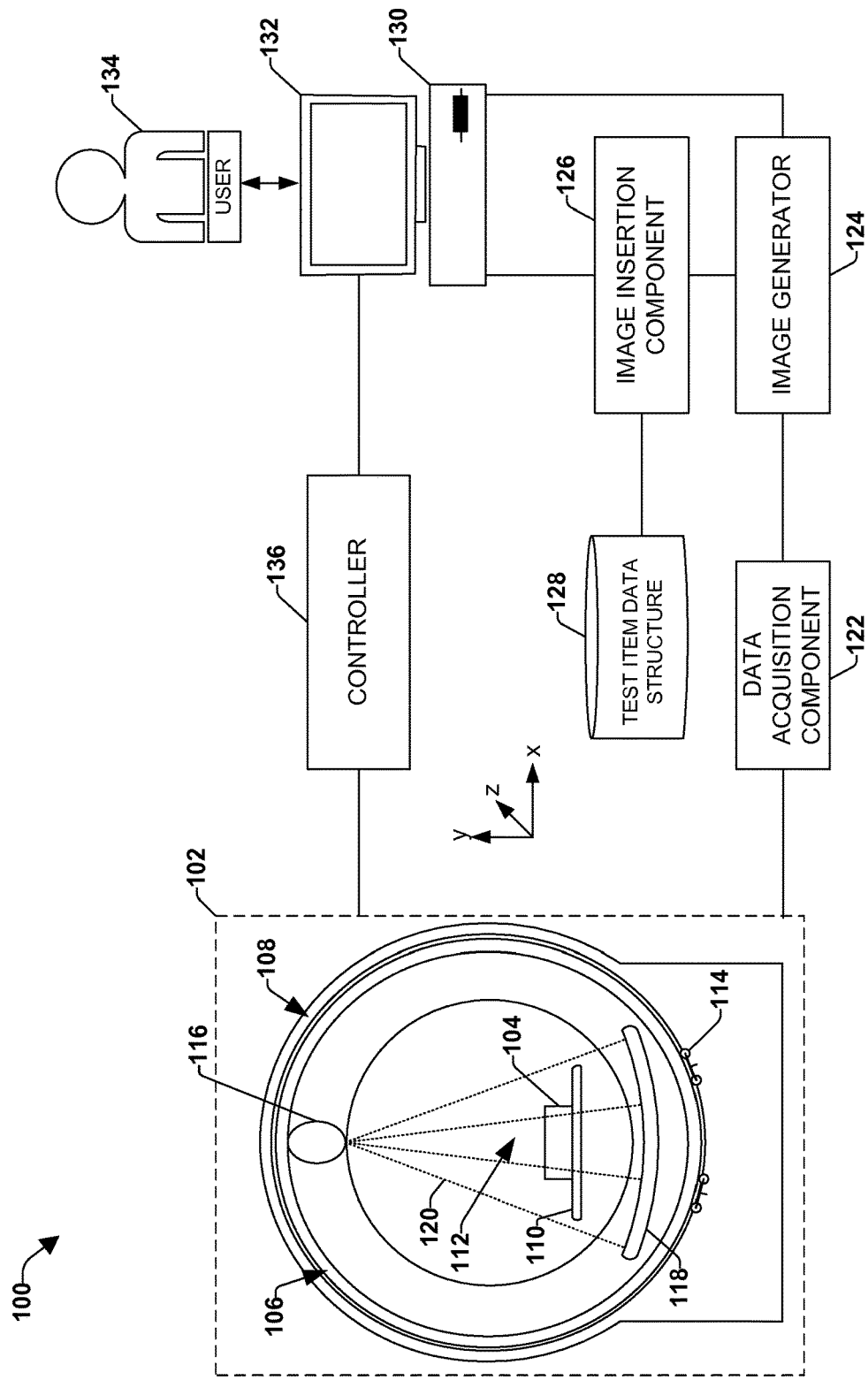
FIG. 1 is a schematic block diagram illustrating an example environment where an imaging system such as described herein may be implemented.

FIG. 1 illustrates an example environment 100 of an imaging system that utilizes radiation to image an article as provided for herein. It may be appreciated that the example environment 100 merely provides an example arrangement and is not intended to be interpreted in a limiting manner, such as necessarily specifying the location, inclusion, and/or relative position of the components depicted therein. By way of example, the data acquisition component 122 may be part of the detector array 118. Though illustrated as comprising two separate structures, in a possible example, an image insertion component 126 may be comprised as a part of a terminal 130.

In the example environment 100, an examination unit 102 of the imaging system is configured to examine articles (e.g., bags, suitcases, patients, etc.), such as an article 104. By way of example, the examination unit 102 may be configured to examine a series of bags placed on a conveyor belt and conveyed through the imaging system.

The examination unit 102 can comprise a rotating gantry 106 and a (stationary) support structure 108 (e.g., which may encase and/or surround at least a portion of the rotating gantry 106 (e.g., as illustrated with an outer, stationary ring, surrounding an outside edge of an inner, rotating ring)). The article 104 can be placed on a support article 110 of the examination unit 102, such as a bed or conveyor belt, for example, and may be conveyed or translated into an examination region 112 (e.g., a hollow bore in the rotating gantry 106) configured to selectively receive the article 104. The rotating gantry 106 can be rotated about the article 104 during the examination and/or moved relative to the article 104 by a rotator 114, such as a motor, drive shaft, chain, roller truck, etc.

The rotating gantry 106 may surround a portion of the examination region 112 and may comprise a radiation source 116 (e.g., an ionizing radiation source such as an x-ray source, gamma-ray source, etc.) and a detector array 118 that is mounted on a substantially diametrically opposite side of the rotating gantry 106 relative to the radiation source 116. In this way, a relative position of the radiation source 116 and the detector array 118 (e.g., the position of the radiation source(s) 116 relative to the detector array 118) may be maintained during an examination of the article 104, for example.

During the examination of the article 104, the radiation source 116 emits fan and/or cone shaped radiation 120 from a focal spot(s) of the radiation source 116 (e.g., a region within the radiation source 116 from which radiation 120 emanates) into the examination region 112. It may be appreciated that such radiation 120 may be emitted substantially continuously and/or may be emitted intermittently or periodically (e.g., a brief pulse of radiation is emitted followed by a resting period during which the radiation source 116 is not activated).

As the emitted radiation 120 traverses the article 104, the radiation 120 may be attenuated differently by different aspects of the article 104. Because different aspects attenuate different percentages of the radiation 120, an image(s) of the article 104 may be generated based upon the attenuation, or variations in the number of radiation photons that are detected by the detector array 118. For example, more dense aspects of the article 104, such as a metal plate, may attenuate more of the radiation 120 (e.g., causing fewer radiation photons to strike the detector array 118) than less dense aspects, such as clothing.

Radiation detected by the detector array 118 may be directly converted and/or indirectly converted into analog signals that can be transmitted from the detector array 118 to a data acquisition component 122 operably coupled to the detector array 118. The analog signal(s) may carry information indicative of the radiation detected by the detector array 118 (e.g., such as an amount of charge measured over a sampling period and/or an energy level of detected radiation), and the data acquisition component 122 may be configured to convert the analog signals into digital signals and/or to compile signals that were transmitted within a predetermined time interval, or measurement interval, using various techniques (e.g., integration, photon counting, etc.).

In the example environment 100, an image generator 124 (e.g., or image reconstructor) is configured to receive the projection data that is output by the data acquisition component 122. Such an image generator 124 may be configured to generate one or more images of the article 104 under examination from the projection data using a suitable analytical, iterative, and/or other image generation technique (e.g., backprojection reconstruction, tomosynthesis reconstruction, iterative reconstruction, etc.). In this way, the data is converted from projection space to image space, a domain that may be more understandable by a user 134 viewing the image(s), for example.

It may be appreciated that because the position of the radiation source 116 and/or the detector array 118 change relative to the article 104 during the examination (e.g., due to the rotation of the radiation source 116 and/or detector array 118 about the article 104), volumetric data indicative of the article 104 may be yielded from the information generated by the detector array 118. Accordingly, the image(s) generated by the image generator 124 may be 3D images (e.g., also referred to as volumetric images), for example.

The example imaging system further comprises an image insertion component 126 that may be operably coupled to the image generator 124 and is configured to insert a 3D test image of a test item (e.g., an item not comprised within the article 104 undergoing examination) into a 3D article image to generate a 3D combined image. That is, stated differently, the image insertion component 126 is configured to combine a 3D article image of the article 104, provided by the image generator 124, with a 3D test image of a test item, provided by a test item data structure 128, to generate a 3D combined image that illustrates the test item as comprised within the article 104. By way of example, the image insertion component 126 may be configured to insert a 3D test image of a weapon, explosive, or other threat item into a 3D article image of a benign bag to create a 3D combined image that appears to show a threat item within the bag. In this way, a 3D combined image may be created that tests the ability of an operator to identify a potential threat item without requiring a test bag, actually containing the threat item, to be examined, for example. In a possible example, the image generator 124 may not generate full 3D images but, rather, only portions (e.g., "slices") of 3D images. In such an example, the image insertion component 126 may not be coupled to the image generator 124 but, rather, may be coupled to a terminal 130 that assembles the images received from the image generator 124 and the image insertion component 126.

In the illustrated embodiment, 3D test images of one or more test items are stored in the test item data structure 128, which is operably coupled to the image insertion component 126. In one embodiment, the test item data structure 128 may comprise a plurality of 3D test images respectively representative of one or more test items, and one or more of the 3D test images stored in the test item data structure 128 may be selected for insertion into a 3D article image of the article 104. It may be appreciated that by having a large pool of 3D test images (e.g., respectively representative of a different test item), it may be difficult for a user 134 inspecting images to become accustomed to the test items (e.g., where becoming accustomed to the test items may make identification of the test items easier and thus decreases the value of the 3D combined image as a testing tool or performance measure).

The image insertion component 126 is configured to select a 3D test image of a test item from the test item data structure 128. The selection of the 3D test image of the test item by the image insertion component 126 may be random or may be a function of specified criteria input into the image insertion component 126. For example, based upon a priori knowledge, it may be known that some test items (e.g., targets) and/or classes of test items are more difficult for operators to detect than other test items. Accordingly, test images of test items may be selected by the image insertion component 126 based upon a desired degree of difficulty, desired orientation, frequency, etc. By way of example, a supervisor of a user 134 may desire to test the user 134 on a particular class of test item and/or may desire to specify a degree of difficulty at which to test the user 134. Based upon input from the supervisor, the image insertion component 126 may select a test image (e.g., an image of the test item) that satisfies the specifications of the supervisor and may retrieve a 3D test image of the test item from the test item data structure 128, for example.

The image insertion component 126 is further configured to determine a selection region in the 3D article image of the article 104 into which to insert the 3D test image of the test item. As will be further described in more detail below, the selection region may be determined at random and then verified (e.g., to verify that the selection region does not comprise objects that would make it physically impossible to place the test item in the selection region if the test item was actually concealed within the article 104) and/or the selection region may be determined based upon an image metric, such as a CT value of respective voxels in the 3D image article (e.g., where the CT value is indicative of density information, z-effective information, Compton score, etc.). For example, in one embodiment, the image insertion component 126 is configured identify one or more groups of voxels having an image metric (e.g., such as CT value) that is below a specified threshold, and to define at least one of the one or more groups of voxels as the selection region.

The example environment 100 further comprises a terminal 130, or workstation (e.g., a computer), that may be configured to receive images generated by the image generator 124 and/or synthesized images generated by the image insertion component 126. At least some of the received information/images may be provided by the terminal 130 for display on a monitor 132 to a user 134 (e.g., security personnel, medical personnel, etc.). In this way, the user 134 can inspect the image(s) to identify areas of interest within the article 104 and/or the user 134 can be tested by displaying a combined image(s), for example. The terminal 130 can also be configured to receive user input which can direct operations of the examination unit 102 (e.g., a speed to rotate, a speed and direction of a support article 110, etc.), for example.

In the example environment 100, a controller 136 is operably coupled to the terminal 130. The controller 136 may be configured to control operations of the examination unit 102. By way of example, in one embodiment, the controller 136 may be configured to receive information from the terminal 130 and to issue instructions to the examination unit 102 indicative of the received information (e.g., adjust a speed of a conveyor belt).

Figure 2:
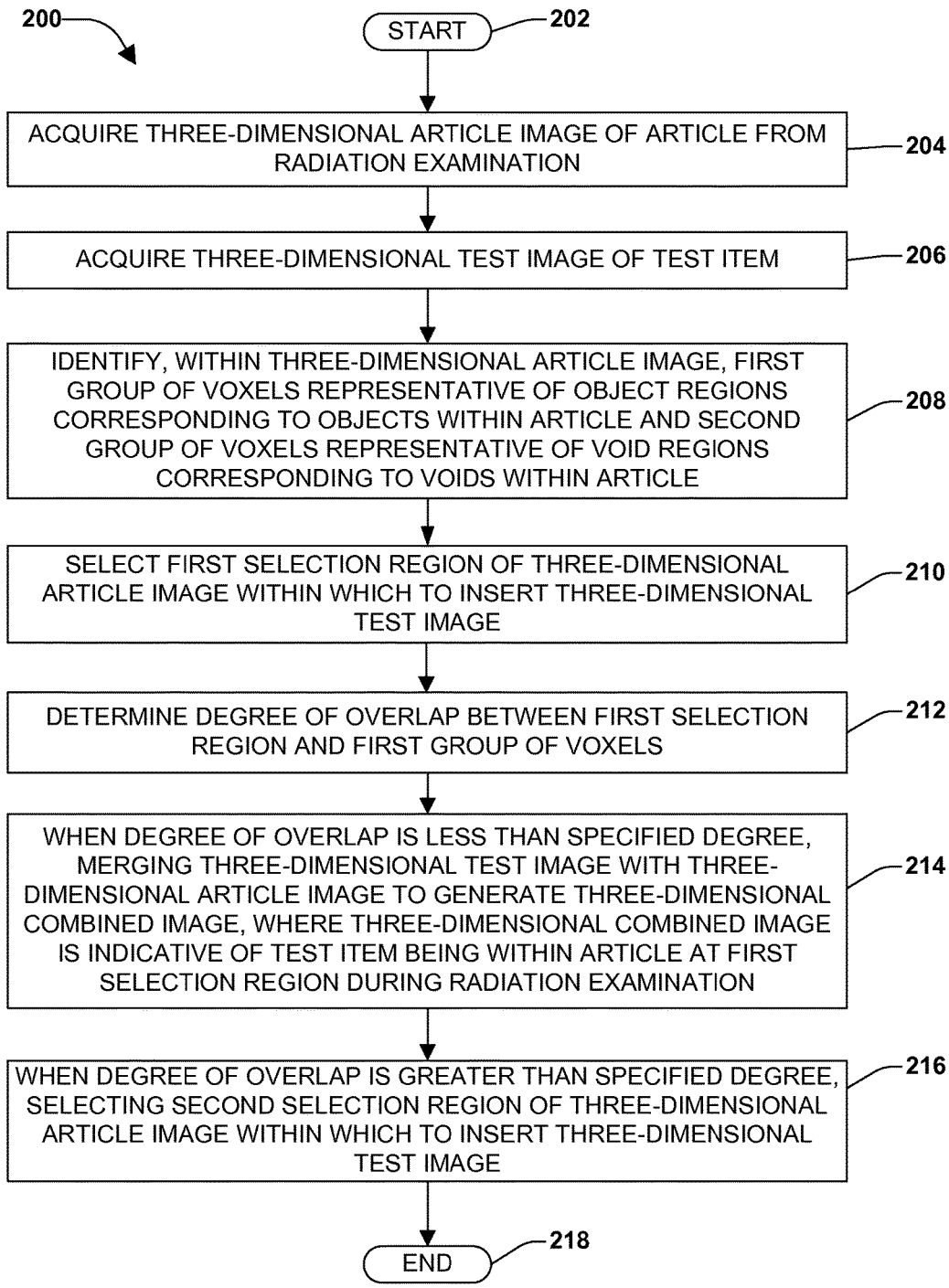
FIG. 2 is a flow chart diagram of an example method for generating a three-dimensional combined image representative of an article undergoing examination and representative of a test item.

FIG. 2 illustrates an example method 200 for generating a 3D combined image representative of an article undergoing a radiation examination and representative of a test item not comprised within the article during the radiation examination. The example method 200 begins at 202, and a 3D article image of an article is acquired from the radiation examination at 204. For example, in an embodiment, a computed-tomography (CT) examination or other radiation examination may be performed on the article and the 3D article image of the article may be derived from the radiation examination using analytic, iterative, or other reconstruction techniques. The 3D article image of the article 104 represents a volume of the article 104 and typically depicts one or more internal or interior aspects of the article 104. For example, where the article 104 under examination is baggage, the 3D article image may depict contents of the baggage.

At 206, in the example method 200, a 3D test image of a test item is acquired. The test item may not be comprised within the article 104, although an end result of the example method 200 may be to produce a 3D combined image that makes it appear as though the test item is comprised within the article 104. In security applications, the test item may be a weapon or other threat item that a user 132 is expected to be able to identify within an image.

At 208 in the example method 200, a first group of voxels representative of object regions corresponding to objects within the article 104 and a second group of voxels representative of void regions corresponding to voids within the article 104 are identified. In an example, the image insertion component 126 can identify voxels that have an image metric that is above or below a specified threshold and can group voxels based upon the image metric, where voxels having an image metric above the threshold are grouped in the first group and voxels having an image metric below the threshold are grouped in the second group.

For example, the image metric can correspond to CT value, which is based upon density information, z-effective information, or other information derivable from projection data generated from the radiation examination. In some embodiments, the CT value for a voxel is proportional to the density and/or atomic number of an object represented by the voxel. For example, high density objects, such as a metal plate, explosive, etc. may be represented by voxels having a higher CT value than lower density objects, such as empty spaces, clothing, etc., which may be represented by voxels having a lower CT value. As will be further appreciated below, the specified threshold may be selected based upon what types of objects are to be effectively considered a void and what types of objects are to be considered objects that the threat item cannot overlap without making the combined image appear unrealistic (e.g., a gun occupying a same space as a heel of a shoe may appear unrealistic, thus making the gun more easily detectable). In some embodiments, the threshold is selected to treat voxels representative of clothing as void regions. In other embodiments, the threshold is selected to treat voxels representative of clothing as object regions.

At 210 in the example method 200, a first selection region of the 3D article image, within which to insert the 3D test image, is selected. In an example, the image insertion component 126 can select the first selection region of the 3D article image at random without information regarding image metrics associated with the 3D article image and/or without information regarding the test image.

In another example, the image insertion component 126 can select the first selection region of the 3D article image based on specified criteria. By way of example, the image insertion component 126 can select the first selection region based on image metrics associated with 3D article image. As an example, the image insertion component 126 can identify clusters of voxels that correspond to the second group of voxels, which are representative of void regions. The first selection region can then be defined (e.g., selected) based upon one or more of these clusters of voxels. In some embodiments, defining the first selection region comprises defining the first selection region as a function of the size and/or shape of the test image of the test item (e.g., to select a cluster of voxels that best approximates the size and/or shape of the test item). In other embodiments, the first selection region can be defined irrespective of the size and/or shape of the test image. For example, the first selection region can be defined as a largest cluster of voxels that correspond to the second group of voxels.

At 212, in the example method 200, a degree of overlap between the first selection region and the first group of voxels is determined. In an example, after the first selection region has been selected, the image insertion component 126 can determine whether the first selection region overlaps the first group of voxels, which are representative of object regions corresponding to objects having a density above a defined threshold, for example. In some examples, the degree of overlap represents a number of voxels of the first group of voxels that are overlapped by the first selection region.

At 214, in the example method 200, when the degree of overlap is less than a specified degree (e.g., when the total number of voxels within the first selection region that are associated with the first group is less than a specified number and/or a percentage of voxels within the first selection region that are associated with the first group is less than a specified percentage), the 3D test image is merged with the 3D article image to generate the 3D combined image, where the 3D combined image is indicative of the test item being within the article 104 at the first selection region during the radiation examination.

In an example, voxels of the 3D article image of the article 104 within the first selection region may be replaced with voxels of the 3D test image of the test item to artificially insert the test item into the article 104. In another example, instead of replacing the voxels of the 3D article image of the article 104, one or more properties of such voxels within the first selection region may be combined with one or more corresponding properties of voxels of the 3D test image of the test item. For example, CT values of one or more voxels of the 3D article image of the article 104 within the first selection region may be combined (e.g., summed) with CT values of one or more voxels of the 3D test image of the test item.

At 216, in the example method 200, when the degree of overlap is greater than the specified degree, a second selection region of the 3D article image within which to insert the 3D test image can be selected. In such an example, the second selection region can be selected in a similar manner as the first selection region was selected. That is, the second selection region can be selected at random or may be selected as a function of specified criteria. The method 200 ends at 218.

FIGS. 3 to 8 provide example illustrations of various 3D images at different stages of the image insertion process. With respect to FIG. 3, an example 3D test image 300 of a test item 302 is illustrated. It will be appreciated that in this example, the test image 300 defines a bounding box (e.g., boundary) of the test item 302. The test image 300 and the test item 302 are not so limited, and in another example, the test image 300 may mimic the size of the test item 302 but not the shape, such as by having a substantially rectangular shape, oval shape, or the like. The 3D test image 300 may be retrieved from the test item data structure 128 (e.g., illustrated in FIG. 1) by the image insertion component 126. In the illustrated example, the test item 302 is a gun, although other threat items and/or non-threat items are also contemplated. In some examples, such as the example illustrated in FIG. 3, the 3D test image 300 can represent more than just the test item 302. That is, the 3D test image 300 can represent voxels not representative of the gun, which may be zeroed-out (such that the voxels are essentially devoid of information and thus represent empty space). In this example, the 3D test image 300 has a cubic shape. In other examples, however, the 3D test image 300 can have a shape that more closely matches a shape of the test item 302, such as by having a gun shape to match the test item 302 (e.g., a gun) in FIG. 3.

FIG. 4 illustrates an example 3D article image 400 of an article 402 (e.g., such as a suitcase) that underwent and/or is presently undergoing a radiation examination. Such a 3D article image 400 may be generated by the image generator 124 and/or obtained by the image insertion component 126, for example. The article 402 comprises one or more object regions 404 corresponding to objects 408, 410 within the article 402. The article 402 comprises one or more void regions 412 corresponding to voids 414 within the article 402 and/or corresponding to portions of the article 402 having an image metric (e.g., CT value) less than the specified threshold. The objects 408, 410 have any number of sizes and shapes. In the illustrated example, a first object 408 is substantially hexahedron-shaped while a second object 410 is substantially cylindrically shaped. The void regions 412 comprise substantially empty space and/or low-attenuation materials, such as clothing, for example.

FIG. 5 illustrates the 3D article image 400 of the article 402 after a first selection region 504 has been selected. In this example, the first selection region 504 is located within the void region 412 of the article image 400. Such a position is not intended to be limiting, however. Rather, in other examples, the first selection region 504 can partially or completely overlap with one or more of the objects 408, 410 of the object regions 404. In addition, in the illustrated example, the first selection region 504 has a cubic shape though, in other examples, the first selection region 504 can have a shape that more closely matches a shape of the test item 302, such as by having a gun shape, for example. In the illustrated example, a degree of overlap between the first selection region 504 and a first group of voxels representative of the object regions 404 corresponding to the objects 408, 410 can be identified.

If the degree of overlap between the first selection region 504 and the first group of voxels is less than a specified degree, the 3D test image 300 may be merged with the 3D article image 400 to form the 3D combined image 600 as shown in FIG. 6.

In some embodiments, the location of voxels of the first group are also considered when determining whether a degree of overlap precludes the selection region as a possible location for inserting the test item. By way of example, in some embodiments, when a 3D test image 300 is merged with a 3D article image 400, a CT value for the 3D combined image is based upon a weighted average of a CT value of a voxel of the 3D article image 400 and a corresponding CT value of a voxel of the 3D test image. In some embodiments, a weight applied to the CT value of the voxel of the 3D article image 400 relative to a weight applied to the corresponding CT value of the voxel of the 3D test image may be a function of the location of respective voxels relative to the selection region. For example, a higher relative weight may be applied to voxels of the 3D article image 400 than to voxels of the 3D test image 300 near an outer boundary of the selection region 504, whereas a higher relative weight may be applied to voxels of the 3D test image 300 than voxels of the 3D article image 400 near an inner core of the selection region 504. Thus, a plurality of voxels of the first group that are located near an outer boundary of the selection region 504 may be able to be blended better in the 3D combined image 600 than a plurality of voxels of the first group that are located near an inner core of the selection region 504.

Referring to FIG. 7, a first selection region 702 may be defined that comprises an outer boundary region 706 and an inner boundary region 708. The first selection region 704 may overlap a portion of the first group of voxels representative of the object regions 404 corresponding to the objects 408, 410. In this example, the first selection region 704 overlaps the second object 410, but, in other examples, the first selection region 704 can overlap either the first object 408 or the second object 410, both the first object 408 and the second object 410, neither the first object 408 nor the second object 410, or other, un-illustrated objects. In this example, a degree of overlap between the first selection region 704 and the first group of voxels can be determined.

In some examples, the determination of the degree of overlap between the first selection region 704 and the first group of voxels comprises determining whether a portion of the first group of voxels that are within the selection region 704 are within an inner boundary region 708 of the first selection region 704. In an example, when the portion of the first group of voxels that are within the inner boundary region 708 of the first selection region 704 does not exceed an inner boundary threshold, the 3D test image 300 can be merged with the 3D article image 400 to form the 3D combined image, such as by inserting the 3D test image 300 into the first selection region 704. As such, the test item 302 of the 3D test image 300 may not overlap the first group of voxels representative of the object regions 404. Thus, the degree of overlap between the selection region 704 and voxels of the first group does not necessarily preclude the 3D test image 300 from being merged with the 3D article image 400 at the selection region if the overlap occurs within an outer boundary region 706 and/or occurs, to a lesser extent, within an inner boundary region 708. In an example, the inner boundary region 708 can be defined as a region within the first selection region 704 that substantially matches a size and/or a shape of the test item 302. In the illustrated example, the inner boundary region 708 substantially mimics the shape and/or boundary of the test item 302 (e.g., by having a gun shape) while in other examples, the inner boundary region 708 may mimic the size of the test item 302 but not the shape, such as by having a substantially rectangular shape, oval shape, or the like. In an example, the outer boundary region 704 can be defined as a region within the first selection region 704 that forms a perimeter partially or completely around the inner boundary region 708. In some examples, the outer boundary region 704 may comprise artifacts related to the test item 302. Voxels within the inner boundary region (e.g., representative of the test item) and voxels within the outer boundary region 704 (e.g., representative of artifacts) are both combined with the voxels of the 3D article image 400, in some embodiments, to enable the test item 302 to better assimilate within the 3D article image 400 (e.g., making the test image 302 appear as though it was present within the article during the examination of the article).

When the portion of the first group of voxels that are within the inner boundary region 708 of the first selection region 704 exceeds the inner boundary threshold, the 3D test image 300 may not be merged with the 3D article image 400 because of a potentially noticeable mismatch between the test item 302 and the portion of the first group of voxels (e.g., the second object 410), which increases a possibility of the operator detecting the presence of an image manipulation.

FIG. 8 illustrates the 3D article image 400 of the article 402 after the second selection region 804 has been selected because the degree of overlap (illustrated in FIG. 7) between the first selection region 704 and the first group of voxels is greater than the specified degree and because of the location of the voxels of the first group relative to the first selection region (e.g., the number of voxels within the inner boundary 708 exceeds an inner boundary threshold). In an example, the second selection region 804 can be selected in a similar manner as described above with respect to the first selection region 504, 704. That is, the second selection region 804 can be selected at random or based on specified criteria.

FIG. 9 is a flow diagram illustrating an example embodiment 900 of generating a 3D combined image representative of an article undergoing a radiation examination and representative of a test item not comprised within the article during the radiation examination. The example embodiment 900 begins at 902. At 904, a 3D article image (e.g., the 3D article image 400 illustrated in FIG. 4) is acquired.

At 906, a 3D test image (e.g., 3D test image 300 illustrated in FIG. 3) of a test item (e.g., test item 302) is acquired. In an example, the 3D test image can be acquired from a test item data structure (e.g., test item data structure 128 illustrated in FIG. 1). In some examples, the test item comprises a threat item.

At 908, a first group of voxels representative of object regions and a second group of voxels representative of void regions are identified. In an example, the identification comprises selecting a specified threshold for object regions and void regions within the 3D article image. The first group of voxels, representative of the object regions (e.g., object regions 404 illustrated in FIG. 4), can have an image metric that is above the specified threshold. The second group of voxels, representative of the void regions (e.g., void region 412 illustrated in FIG. 4), can have an image metric that is below the specified threshold. According to some examples, the image metric can be based on density information or other information (e.g., z-effective, Compton score, etc.).

At 910, a first selection region of the 3D article image can be selected. The first selection region (e.g., first selection region 504 illustrated in FIG. 5) can be selected at random and/or based upon specified criteria. In some examples, the first selection region comprises an outer boundary region (e.g., outer boundary region 706 illustrated in FIG. 7) and an inner boundary region (e.g., inner boundary region 708).

At 912, in an example, the 3D test image can be inserted within the first selection region. It will be appreciated that in some examples, the 3D test image can be inserted within the first selection region following the selection of the first selection region, as illustrated in FIG. 9. In other examples, the 3D test image may not be inserted within the first selection region until later (e.g., after determining a degree of overlap between the first selection region and the first group of voxels).

At 914, the embodiment 900 comprises determining whether the first selection region lies on the second group of voxels. In some examples, a majority of the first selection region may lie on (e.g., overlap) the second group of voxels. In such an example, since the second group of voxels are representative of a void region, the first selection region may lie on a void region.

FIG. 10 is a flow diagram illustrating an example embodiment 1000 that follows the embodiment 900 illustrated in FIG. 9. In this example, the example embodiment 1000 can follow the determination at 914 of whether the first selection region lies on (e.g., overlaps) the second group of voxels. The first selection region may at least partially lie on the first group of voxels. In such an example, the first selection region may not lie on (e.g., completely overlap) the second group of voxels (e.g., NO at 914).

At 1002, the embodiment 1000 comprises determining whether the overlap between the first selection region and the first group of voxels is less than a specified degree. In an example, when the overlap is less than the specified degree (e.g., YES at 1002), the 3D test image of the test item can be merged with the 3D article image. In this example, the 3D test image of the test item can be inserted into the first selection region. Voxels of the 3D test image, comprising the test item, can replace voxels of the 3D article image at the location of the first selection region so as to artificially insert the 3D test image into the 3D article image. In another embodiment, the 3D test image of the test item may be overlaid on top of the 3D article image at the location of the first selection region (e.g., merging, summing, averaging, etc. voxels of the 3D test image with voxels of the 3D article image).

In some examples, overlapping voxels of the 3D test image that overlap the first group of voxels can be weighted. In such an example, these overlapping voxels (e.g., of the 3D test image) can be weighted with the portion(s) of the first group of voxels (e.g., overlapped voxels) rather than replacing the portion of the first group of voxels. For example, one or more properties of these overlapping voxels of the 3D test image can be combined with one or more corresponding properties of the portion(s) of the first group of voxels that is overlapped. In an example, CT values of the 3D test image may be combined (e.g., summed) with CT values of the portion of the first group of voxels that are overlapped.

At 1006, when the overlap is greater than the specified degree (e.g., NO at 1002), the embodiment 1000 comprises determining whether the portion of the first group of voxels that is overlapped by the first selection region is within the inner boundary region (e.g., inner boundary region 708) of the first selection region. In such an example, the first selection region 704 has the inner boundary region and an outer boundary region (e.g., outer boundary region 706). When the 3D test image is inserted into the first selection region, the outer boundary region generally corresponds to a void region while the inner boundary region generally corresponds to the test item. If the portion of the first group of voxels is not within the inner boundary region (e.g., NO at 1006), then the 3D test image of the test item can be merged with the 3D article image (e.g., at 1004).

At 1008, if the portion of the first group of voxels is within the inner boundary region of the first selection region (e.g., YES at 1006), then a second selection region (e.g., second selection region 804 illustrated in FIG. 8) is selected. Once the second selection region has been selected, the method can begin again at 912 in FIG. 9.

FIG. 11 is a flow diagram illustrating an example embodiment 1100 that follows 914 illustrated in FIG. 10. In this example, the example embodiment 1100 can follow the determination that the first selection region lies on the second group of voxels (e.g., YES at 914 in FIG. 10) representative of void regions corresponding to voids within the article.

At 1102, the embodiment 1100 comprises calculating a distance from a boundary of a test item 1304 to a nearest object below the boundary of the test item 1304. Referring to FIG. 13, an example 3D article image 1300 is illustrated. The example 3D article image 1300 comprises a 3D test image 1302 of a test item 1304. The 3D test image 1302 is inserted within a first selection region 1306. A distance can be calculated from the boundary of the test item 1304 to the nearest object below the first selection region 1306. In this example, the nearest object below the first selection region 1306 is the first object 408. In an example, the nearest object below the first selection region 1306 may comprise a part of the article (e.g. a test bag), such as an inner wall or surface of the test bag, within which the 3D article image 1300 is inserted or may comprise an object disposed within the article (e.g., clothing, books, etc.). Moreover, in some examples, the boundary referred to herein may be a lower boundary or gravitational bottom of the test item 1304 that is nearest to a source of attraction (e.g., a source of the gravitational pull) so as to provide an appearance of a gravitationally stable resting location. Such a gravitational bottom may be dependent upon the placement of the test item 1304 within the 3D article image 1300 and the orientation of the article during the examination, for example.

At 1104, the embodiment 1100 comprises adjusting a y-value of the test item 1304 to adjust a distance between the test item 1304 and the nearest object (e.g., to make it appear as though the test item is resting on the object to account for gravity). As illustrated in FIG. 13, the test item 1304 is located a distance from the nearest object (e.g., the first object 408). To adjust this distance, the y-value of the test item 1304 can be adjusted. As such, a position of the test item 1304 can be adjusted with respect to the nearest object (e.g., the first object 408), with the test item 1304 being adjusted downwardly towards the first object 408. In such an example, a distance between the test item 1304 and the nearest object in the y-direction is reduced, and may be zero.

At 1106, the embodiment 1100 comprises adjusting an x-value of the test item 1304 to adjust a distance between the test item 1304 and the nearest object (e.g., to further conceal the test item). Referring to FIGS. 13 and 14, the first selection region 1306, comprising the 3D test image 1302 of the test item 1304, can be located a distance from the nearest object (e.g., the second object 410) along the x-direction. To adjust this distance, the x-value of the test item 1304 can be adjusted such that the 3D test image 1302 is located above the nearest object. In this example, the test item 1304 is adjusted along the x-direction (e.g., left and right directions in FIGS. 13 and 14). As such, a distance between the test item 1304 and the nearest object in the x-direction is reduced, and may be zero such that the test item 1304 may be in contact with, abutting against, etc. the nearest object.

At 1108, the embodiment 110 comprises determining a number of voxels within the first group of voxels that abut a boundary of the test item 1304. It is to be appreciated that the boundary of the test item 1304 may, in some examples, comprise the lower boundary (e.g., the gravitational bottom of the test item 1304), and/or a side boundary. Referring to FIG. 14, after adjusting the y-value and x-value of the test item 1304, the test item 1304 can abut (e.g., contact) the first group of voxels representative of the object regions 404 corresponding to the objects 408, 410 (e.g., to make it appear as though the test item is resting upon other objects 408, 410 (e.g., as opposed to floating in space). In this example, the voxels within the first group of voxels that abut a boundary of the test item 1304 are illustrated as abutment locations 1400.

FIG. 12 is a flow diagram illustrating an example embodiment 1200 that follows the embodiment 1100 illustrated in FIG. 11. In this example, the example embodiment 1100 can follow the determination at 1108 of the number of voxels within the first group of voxels that abut the boundary of the test item 1304.

At 1202, the embodiment 1200 comprises determining whether the number of voxels within the first group of voxels that abut the boundary of the test item 1304 is greater than a threshold. The threshold comprises any number of abutment locations 1400 between the first group of voxels and the boundary of the test item 1304. In an example, the threshold comprises three or more abutment locations 1400. Determining the number of abutment locations 1400 provides for a 3D combined image that is more realistic. More particularly, in an example when there are zero abutment locations 1400, the first selection region 1306, and, thus, the test item 1304, is located within the void region 412, such that the first selection region 1306 (and, thus, the test image 300 of the test item 1304) does not contact the object regions 404. Such a location for the test item 1304 may not be realistic, as the test item 1304 would normally be supported on one or more objects 408, 410. Accordingly, ensuring that a minimum number (e.g., threshold) of abutment locations 1400 are present reduces a possibility of the operator detecting the presence of an image manipulation.

At 1204, when the number of voxels within the first group of voxels that abut the boundary of the test item 1304 is greater than the threshold (e.g., YES at 1202), the embodiment 1200 comprises determining whether the abutment locations 1400 are evenly distributed around a center of mass of the test item 1304. Despite the threshold number of abutment locations 1400 being met, the position of the abutment locations 1400 with respect to the first selection region 1306 and the test item 1304 can indicate whether the 3D combined image is realistic. In an example, the abutment locations 1400 may not be evenly distributed around the center of mass of the test item 1304, such as by being concentrated at a single location (e.g., bottom corner) of the test item 1304. In such an example, it may not be realistic for the test item 1304 to be supported on the object(s) 408, 410, as the test item 1304 would likely fall over and/or be unable to maintain such a position.

On the other hand, when the abutment locations 1400 are evenly distributed around the center of mass of the test item 1304, such as in the example of FIG. 14, it is more likely for the test item 1304 to maintain such a position, as the test item 1304 is adequately supported about its center of mass. Accordingly, ensuring that a relatively even distribution of abutment locations 1400 about the center of mass of the test item 1304 reduces a possibility of the operator detecting the presence of an image manipulation. When the abutment locations 1400 are evenly distributed around a center of mass of the test item 1304 (e.g., YES at 1204), the embodiment 1200 comprises merging the 3D test image 1302 with the 3D article image (e.g., at 1206).

At 1208, when the number of voxels within the first group of voxels that abut the boundary of the test item 1304 is less than the threshold (e.g., NO at 1202) or the abutment locations 1400 are not evenly distributed around the center of mass of the test item 1304 (e.g., NO at 1204), the embodiment 1200 comprises adjusting a z-value of the test item 1304 to adjust a distance between the test item 1304 and the nearest object. Referring to FIGS. 13 and 14, the first selection region 1306, comprising the 3D test image 1302, can be located a distance from the nearest object along the z-direction. To adjust this distance, the z-value of the test item 1304 can be adjusted such that the 3D test image 1302 is located above and/or in contact with the nearest object. In this example, the test item 1304 is adjusted along the z-direction (e.g., into and out of the page in FIGS. 13 and 14). As such, a distance between the test item 1304 and the nearest object in the z-direction is reduced, and may be zero.

At 1210, the embodiment 1200 comprises determining whether the number of voxels within the first group of voxels that abut the test item 1304 is greater than a threshold. As described above with respect to 1202, the threshold comprises any number of (e.g., two or more) abutment locations 1400 between the first group of voxels and the boundary of the test item 1304. When the number of voxels within the first group of voxels that abut the boundary of the test item 1304 is greater than the threshold (e.g., YES at 1210), the embodiment 1200 comprises determining (e.g., at 1204) whether the abutment locations 1400 are evenly distributed around a center of mass of the test item 1304. At 1212, when the number of voxels within the first group of voxels that abut the test item 1304 is less than the threshold (e.g., NO at 1210), then a second selection region is selected.

FIG. 15 illustrates an example method 1500 for generating a 3D combined image representative of an article undergoing a radiation examination and representative of a test item not comprised within the article during the radiation examination. The example method 1500 begins at 1502. At 1504, a 3D article image of an article is acquired via the radiation examination. In an example, a computed-tomography (CT) examination or other radiation examination may be performed on the article and the 3D article image of the article may be derived from the radiation examination using analytic, iterative, or other reconstruction techniques.

At 1506, in the example method 1500, a 3D test image of a test item is acquired. The test item may not be comprised within the article 104, although an end result of the example method 1500 may be to produce a 3D combined image that appears to illustrate that the test item is comprised within the article 104.

At 1508, in the example method 1500, a first group of voxels representative of object regions corresponding to objects within the article 104 and a second group of voxels representative of void regions corresponding to voids within the article 104 are identified. In an example, the image insertion component 126 can identify voxels that have an image metric that is above or below a specified threshold. The image metric, such as CT values, can be based on density information or other information (e.g., z-effective, Compton score, etc.) derivable from the 3D article image of the article 104. The first group of voxels, representative of object regions corresponding to objects, has an image metric that is above the specified threshold. The second group of voxels, representative of void regions corresponding to voids, has an image metric that is below the specified threshold.

At 1510, in the example method 1500, a first selection region of the 3D article image within which to insert the 3D test image is selected. In an example, the image insertion component 126 can select the first selection region of the 3D article image at random or based on specified criteria.

At 1512, in the example method 1500, a degree of overlap between the first selection region and the first group of voxels is determined. In an example, after the first selection region has been selected, the image insertion component 126 can determine whether the first selection region overlaps the first group of voxels, which are representative of the object regions corresponding to objects.

At 1514, in the example method 1500, when the degree of overlap is less than a specified degree, a number of voxels within the first group of voxels that abut the test item 1304 can be determined. In an example, the number of voxels within the first group of voxels that abut the test item 1304 comprise one or more abutment locations 1400. That is, the abutment locations 1400 represent locations in which the first group of voxels abut (e.g., contact) the test item 1304. In this example, the first group of voxels are representative of object regions corresponding to objects within the article. Accordingly, an abutment location 1400 may be representative of the test item 1304 (e.g., when inserted into the first selection region) abutting one or more of the objects, such that the test item 1304 is supported by one or more of the objects.

At 1516, in the example method 1500, when the number of voxels that abut the test item 1304 exceeds a threshold, the 3D test image can be merged with the 3D article image to generate the 3D combined image, where the 3D combined image is representative of the test item being within the article at the first selection region during radiation examination. The threshold comprises any number (e.g., two or more) of abutment locations 1400 between the first group of voxels and the test item 1304. In an example, the threshold comprises three or more abutment locations 1400. As such, when the number of voxels exceeds this threshold (e.g., three abutment locations 1400 or points of contact), the 3D test image is merged with the 3D article image, such as by inserting the 3D test image into the first selection region. The method ends at 1518.

FIG. 16 illustrates an example method 1600 for generating a 3D combined image representative of an article undergoing a radiation examination and representative of a test item not comprised within the article during the radiation examination. The example method 1600 begins at 1602. At 1604, a 3D article image of an article is acquired via the radiation examination. In an example, a computed-tomography (CT) examination or other radiation examination may be performed on the article and the 3D article image of the article may be derived from the radiation examination using analytic, iterative, or other reconstruction techniques.

At 1606, in the example method 1600, a 3D test image of a test item is acquired. The test item may not be comprised within the article 104, although an end result of the example method 1600 may be to produce a 3D combined image that appears to illustrate that the test item is comprised within the article 104.

At 1608, in the example method 1600, a first group of voxels representative of object regions corresponding to objects within the article 104 and a second group of voxels representative of void regions corresponding to voids within the article 104 are identified. The first group of voxels, representative of object regions corresponding to objects, has an image metric that is above the specified threshold. The second group of voxels, representative of void regions corresponding to voids, has an image metric that is below the specified threshold.

At 1610, in the example method 1600, a first selection region of the 3D article image within which to insert the 3D test image is selected. In an example, the image insertion component 126 can select the first selection region of the 3D article image at random or based on specified criteria.

At 1612, the example method 1600 comprises determining whether a portion of the first group of voxels are within an outer boundary region of the first selection region or an inner boundary region of the first selection region. In some examples, the inner boundary region can correspond to a shape of the test item 302 while the outer boundary region corresponds to a void region surround the test item 302.

At 1614, when a portion of the first group of voxels are within the outer boundary region of the first selection region, the example method 1600 comprises merging the 3D test image with the 3D article image to generate a 3D combined image, where the 3D combined image is representative of the test item being within the article at the first selection region during the radiation examination. In an example, when the portion of the first group of voxels are within the outer boundary region and not the inner boundary region, the 3D test image is merged with the 3D article image to form the 3D combined image. The method ends at 1616.

Still another embodiment involves a computer-readable medium comprising processor-executable instructions configured to implement one or more of the techniques presented herein. An example computer-readable medium that may be devised in these ways is illustrated in FIG. 17, wherein the implementation 1700 comprises a computer-readable medium 1702 (e.g., a flash drive, CD-R, DVD-R, application-specific integrated circuit (ASIC), field-programmable gate array (FPGA), a platter of a hard disk drive, etc.), on which is encoded computer-readable data 1704. This computer-readable data 1704 in turn comprises a set of computer instructions 1706 configured to operate according to one or more of the principles set forth herein. In an embodiment 1700, the processor-executable instructions 1706 may be configured to perform a method 1708, such as at least some of the example methods 200 of FIG. 10, 1500 of FIG. 15, and/or 1600 of FIG. 16, for example. In another such embodiment, the processor-executable instructions 1706 may be configured to implement a system, such as at least some of the exemplary environment 100 of FIG. 1. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different [or identical] channels).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. A method for generating a three-dimensional combined image representative of an article undergoing a radiation examination and representative of a test item not comprised within the article during the radiation examination, comprising:
   acquiring a three-dimensional article image of the article via the radiation examination;
   acquiring a three-dimensional test image of the test item;
   identifying within the three-dimensional article image:
      a first group of voxels representative of object regions corresponding to objects within the article, wherein the identifying the first group of voxels comprising determining that first image metrics of the first group of voxels are above a specified threshold; and
      a second group of voxels representative of void regions corresponding to voids within the article, wherein the identifying the second group of voxels comprising determining that second image metrics of the second group of voxels are below the specified threshold,
   wherein the first image metrics comprise values indicative of one or more of a density of the objects and an atomic number of the objects, and wherein the second image metrics comprise values indicative of one or more of a density of the voids and an atomic number of the voids;
   selecting a first selection region of the three-dimensional article image within which to insert the three-dimensional test image;

determining a degree of overlap between the first selection region and the first group of voxels;

merging, responsive to the degree of overlap being less than a specified degree, the three-dimensional test image with the three-dimensional article image to generate the three-dimensional combined image, where the three-dimensional combined image is representative of the test item being within the article at the first selection region during the radiation examination; and selecting, responsive to the degree of overlap being greater than the specified degree, a second selection region of the three-dimensional article image within which to insert the three-dimensional test image.

2. The method of claim 1, the determining a degree of overlap comprising determining whether a portion of the first group of voxels are within an outer boundary region of the first selection region or an inner boundary region of the first selection region.

3. The method of claim 2, the merging comprising merging the three-dimensional test image with the three-dimensional article image when the portion of the first group of voxels are within the outer boundary region of the first selection region.

4. The method of claim 2, comprising not merging the three-dimensional test image with the three-dimensional article image when the portion of the first group of voxels are within the inner boundary region of the first selection region.

5. The method of claim 1, the selecting comprising selecting the first selection region at random.

6. The method of claim 1, the selecting comprising identifying the first selection region based on a location, within the three-dimensional article image, of voxels corresponding to at least some of the second group of voxels.

7. The method of claim 1, the selecting comprising:
identifying a cluster of voxels corresponding to the second group of voxels; and
defining the first selection region based upon the cluster of voxels.

8. The method of claim 1, the merging comprising determining a number of voxels within the first group of voxels that abut the test item.

9. The method of claim 1, the test item comprising a threat item.

10. The method of claim 1, the merging comprising merging the three-dimensional test image with the three-dimensional article image in real time.

11. The method of claim 1, the acquiring a three-dimensional test image comprising acquiring the three-dimensional test image from a test item data structure.

12. A method for generating a three-dimensional combined image representative of an article undergoing a radiation examination and representative of a test item not comprised within the article during the radiation examination, comprising:
acquiring a three-dimensional article image of the article via the radiation examination;
acquiring a three-dimensional test image of the test item;
identifying within the three-dimensional article image:
a first group of voxels representative of object regions corresponding to objects within the article, wherein the identifying the first group of voxels comprising determining that first image metrics of the first group of voxels are above a specified threshold; and
a second group of voxels representative of void regions corresponding to voids within the article, wherein the identifying the second group of voxels comprising determining that second image metrics of the second group of voxels are below the specified threshold, wherein the first image metrics comprise values indicative of one or more of a density of the objects and an atomic number of the objects, and wherein the second image metrics comprise values indicative of one or more of a density of the voids and an atomic number of the voids;

selecting a first selection region of the three-dimensional article image within which to insert the three-dimensional test image;

determining a degree of overlap between the first selection region and the first group of voxels;

determining, responsive to determining that the degree of overlap is less than a specified degree, a number of voxels within the first group of voxels that abut the first selection region; and merging, responsive to determining that the number of voxels exceeds a threshold, the three-dimensional test image with the three-dimensional article image to generate the three-dimensional combined image, where the three-dimensional combined image is representative of the test item being within the article at the first selection region during the radiation examination.

13. The method of claim 12, the determining a degree of overlap comprising determining whether a portion of the first group of voxels are within an outer boundary region of the first selection region or an inner boundary region of the first selection region.

14. The method of claim 13, the merging comprising merging the three-dimensional test image with the three-dimensional article image when the portion of the first group of voxels are within the outer boundary region of the first selection region.

15. The method of claim 13, comprising not merging the three-dimensional test image with the three-dimensional article image when the portion of the first group of voxels are within the inner boundary region of the first selection region.

16. A method for generating a three-dimensional combined image representative of an article undergoing a radiation examination and representative of a test item not comprised within the article during the radiation examination, comprising:
acquiring a three-dimensional article image of the article via the radiation examination;
acquiring a three-dimensional test image of the test item;
identifying within the three-dimensional article image:
a first group of voxels representative of object regions corresponding to objects within the article, wherein the identifying the first group of voxels comprising determining that first image metrics of the first group of voxels are above a specified threshold; and
a second group of voxels representative of void regions corresponding to voids within the article, wherein the identifying the second group of voxels comprising determining that second image metrics of the second group of voxels are below the specified threshold, wherein the first image metrics comprise values indicative of one or more of a density of the objects and an atomic number of the objects, and wherein the second image metrics comprise values indicative of one or more of a density of the voids and an atomic number of the voids;

selecting a first selection region of the three-dimensional article image within which to insert the three-dimensional test image;

determining whether a portion of the first group of voxels are within an outer boundary region of the first selection region or an inner boundary region of the first selection region; and when the portion of the first group of voxels are within the outer boundary region of the first selection region, merging the three-dimensional test image with the three-dimensional article image to generate the three-dimensional combined image, where the three-dimensional combined image is representative of the test item being within the article at the first selection region during the radiation examination.

17. The method of claim 16, the selecting comprising selecting the first selection region at random.

18. The method of claim 16, the selecting comprising identifying the first selection region based on a location, within the three-dimensional article image, of voxels corresponding to at least some of the second group of voxels.

19. The method of claim 16, the selecting comprising:
identifying a cluster of voxels corresponding to the second group of voxels; and
defining the first selection region based upon the cluster of voxels.

* * * * *